US012788818B2

(12) United States Patent
Müller-Lierheim

(10) Patent No.: US 12,788,818 B2
(45) Date of Patent: Nov. 10, 2026

(54) HYALURONIC ACID-BASED FORMULATIONS FOR TREATMENT AND PREVENTION OF OCULAR HYPERTENSION AND GLAUCOMA

(71) Applicant: I.COM MEDICAL GMBH, Munich (DE)

(72) Inventor: Wolfgang Georg Konrad Müller-Lierheim, Munich (DE)

(73) Assignee: I.COM MEDICAL GMBH, Munich (DE)

( * ) Notice: Subject to any disclaimer, the term of this patent is extended or adjusted under 35 U.S.C. 154(b) by 814 days.

(21) Appl. No.: 18/002,682

(22) PCT Filed: Jun. 21, 2021

(86) PCT No.: PCT/IB2021/000412
§ 371 (c)(1),
(2) Date: Dec. 21, 2022

(87) PCT Pub. No.: WO2021/260427
PCT Pub. Date: Dec. 30, 2021

(65) Prior Publication Data

US 2023/0233687 A1 Jul. 27, 2023

Related U.S. Application Data

(60) Provisional application No. 63/041,937, filed on Jun. 21, 2020.

(51) Int. Cl.

| | |
|---|---|
| ***A61K 47/36*** | (2006.01) |
| ***A61K 9/00*** | (2006.01) |
| ***A61K 9/08*** | (2006.01) |
| ***A61K 31/4535*** | (2006.01) |
| ***A61K 31/5377*** | (2006.01) |
| ***A61K 31/557*** | (2006.01) |
| ***A61K 31/5575*** | (2006.01) |
| ***A61K 38/13*** | (2006.01) |
| ***A61K 47/26*** | (2006.01) |
| ***A61P 27/02*** | (2006.01) |
| ***A61P 27/06*** | (2006.01) |
| ***A61P 29/00*** | (2006.01) |

(52) U.S. Cl.
CPC ............ *A61K 47/36* (2013.01); *A61K 9/0048* (2013.01); *A61K 9/08* (2013.01); *A61K 31/4535* (2013.01); *A61K 31/5377* (2013.01); *A61K 31/557* (2013.01); *A61K 31/5575* (2013.01); *A61K 38/13* (2013.01); *A61K 47/26* (2013.01); *A61P 27/02* (2018.01); *A61P 27/06* (2018.01); *A61P 29/00* (2018.01)

(58) Field of Classification Search
CPC ...................................................... A61K 47/36
See application file for complete search history.

(56) References Cited

U.S. PATENT DOCUMENTS

| | | | | |
|---|---|---|---|---|
| 8,680,078 | B2 * | 3/2014 | Aleo | A61K 31/5377 514/530 |
| 2012/0122976 | A1 | 5/2012 | Holzer | |
| 2014/0228364 | A1 * | 8/2014 | Hadj-Slimane | A61P 27/02 514/622 |
| 2021/0077523 | A1 | 3/2021 | Müller-Lierheim et al. | |
| 2021/0145862 | A1 | 5/2021 | Müller-Lierheim et al. | |
| 2021/0369764 | A1 | 12/2021 | Müller-Lierheim et al. | |
| 2023/0241096 | A1 | 8/2023 | Müller-Lierheim et al. | |
| 2023/0338541 | A1 | 10/2023 | Müller-Lierheim | |

FOREIGN PATENT DOCUMENTS

| | | |
|---|---|---|
| CN | 103957887 A | 7/2014 |
| EP | 0224987 | 6/1987 |
| EP | 2 567 689 | 3/2013 |
| JP | 62-129226 | 6/1987 |
| JP | 2005-508866 | 4/2005 |
| KR | 10-2012-0047851 A | 5/2012 |
| WO | WO 02/100437 | 12/2002 |
| WO | WO-2013/037479 A1 | 3/2013 |
| WO | WO 2018/069763 | 4/2018 |
| WO | WO 2019/202015 | 10/2019 |
| WO | WO 2019/202017 | 10/2019 |

(Continued)

OTHER PUBLICATIONS

Dogru, M. et al. "The Effect of High Molecular Weight Hyaluronic Acid and Latanoprost Eyedrops on Tear Functions and Ocular Surface Status in C57/BL6 Mice" *Journal of Clinical Medicine*, Jan. 9, 2023, pp. 1-13, vol. 12, No. 544.

Higa, K. et al. "Therapeutic Aqueous Humor Concentrations of Latanoprost Attained in Rats by Administration in a Very-High-Molecular-Weight Hyaluronic Acid Eye Drop" *Pharmaceutics*, Apr. 9, 2024, pp. 1-10, vol. 16, No. 523.

Cowman, M.K. et al. "Viscoelastic Properties of Hyaluronan in Physiological Conditions" F1000Research, 2015, 4:622 (13 pages).

*Primary Examiner* — Paul V Ward

(74) *Attorney, Agent, or Firm* — SALIWANCHIK, LLOYD & EISENSCHENK

(57) ABSTRACT

The present invention concerns ophthalmic compositions comprising a combination of hyaluronic acid (HA) as a vehicle, and one or more prostaglandin analogues, such as latanoprost, as an active pharmaceutical ingredient (API), wherein the HA acts as a transporting vehicle (transporter) of the prostaglandin analogue into the eye. The invention also includes methods for the use of such ophthalmic compositions for reduction of intraocular pressure to treat, prevent, and/or delay the onset or recurrence of ocular hypertension and glaucoma. The ophthalmic compositions of the invention have improved stability, improved API solubility, and improved efficacy in reducing intraocular pressure.

17 Claims, No Drawings

(56) References Cited

FOREIGN PATENT DOCUMENTS

| | | |
|---|---|---|
| WO | WO 2020/157570 | 8/2020 |
| WO | WO 2021/250462 | 12/2021 |
| WO | WO 2021/260430 | 12/2021 |

* cited by examiner

HYALURONIC ACID-BASED FORMULATIONS FOR TREATMENT AND PREVENTION OF OCULAR HYPERTENSION AND GLAUCOMA

CROSS-REFERENCE TO RELATED APPLICATIONS

The present application is the U.S. national stage application of International Patent Application No. PCT/IB2021/000412, filed Jun. 21, 2021, which claims the benefit of U.S. Provisional Application Ser. No. 63/041,937, filed Jun. 21, 2020, which is hereby incorporated by reference herein in its entirety, including any figures, tables, nucleic acid sequences, amino acid sequences, or drawings.

BACKGROUND OF THE INVENTION

Eye drops for the topical treatment of ocular hypertension and glaucoma are composed of an active pharmaceutical ingredient (API) with pharmacological activity dissolved or suspended in a vehicle. Potential functions of the vehicle include dissolving or suspending the API, stabilizing the solution during shelf-life of the eye drops and during patient use, prolonging the contact time between the API and the ocular surface, supporting the penetration of the API into the ocular surface, and enhancing the biocompatibility of the eye drops [1, 2].

Most eye drops are aqueous solutions requiring additives, in particular surfactants to dissolve lipophilic APIs. Eye drops need to be sterile; during patient use this can be achieved either by single-use containers (monodoses), bottles with particular dispensers preventing microbial contamination, or by addition of preservatives like benzalkonium chloride. The contact time with the ocular surface can be prolonged by the addition of polymers increasing the viscosity of the solution. Mucoadhesive additives like hyaluronan can, moreover, adhere to the glycocalyx of the apical epithelial cells, thus promoting the contact between the API and the ocular surface. Penetration enhancers weaken the transcellular or paracellular epithelial barrier function, thus enhancing the diffusion of the API into the ocular surface. Salts are added to adjust the osmolarity, and buffers to adjust and stabilize the pH value of the eye drops to a physiological level and to stabilize the eye drops.

Surfactants are capable of replacing the cell-bound mucins in the glycocalyx of the apical epithelial cells and be incorporated in the lipid bilayer forming the cell membrane, and thus compromise the cell barrier function and support the transport of the API through the cell membrane into the cell [3, 4]. Surfactants like benzalkonium chloride (BAK, cetalkonium chloride) and cationic polymers named polyquaternium are still widely used in ophthalmic drugs because they have a combined effect of dissolving the API in the aqueous solution, enhancing its penetration into the ocular surface, and at the same time preserving the solution against microbial growth. These benefits are at the expense of local irritation and disastrous long-term ocular surface disease [5, 6].

Additives such as ethylenediamine tetra acetic sodium salt (EDTA) deprive the tight junctions between the epithelial cells from $Ca^{2+}$ ions and thus weaken the paracellular barrier function of the epithelium.

Currently available APIs for the treatment of ocular hypertension and glaucoma belong to several pharmacological classes, including β-adrenergic blockers (timolol maleate, carteolol, betaxolol), cholinergic agonists, carbonic anhydrase inhibitors (dorzolamide, brinzolamide) or adrenergic receptor blockers (brimonidine). Mechanisms of action for such APIs involve inhibiting the inflow of aqueous humor, enhancing the outflow of aqueous humor, protecting the optic nerves and manipulating the osmotic pressure between plasma and the eyes. These therapies are typically administered as eye drops.

Prostaglandin inhibitors (such as, for example, latanoprost, unoprostone, travoprost, bimatoprost, tafluprost and the like) reduce intraocular pressure (IOP) primarily by increasing aqueous humor drainage through the uveoscleral outflow pathway.

Current eye drops for the treatment of ocular hypertension and glaucoma, including prostaglandin analogues, can cause serious side effects in a significant percentage of patients. These adverse ocular reactions are not only caused by the APIs, but to a large extent by the vehicles used. In clinical studies for regulatory approval and reimbursement, the safety and performance of new topical ophthalmic drugs are frequently tested in comparison to the vehicle only. This strategy allows eliminating the negative effects of the vehicle, brightening the effect of the product.

It would be advantageous to have available an ophthalmic composition capable of reducing intraocular pressure without compromising the ocular surface and its barrier function, and which permits the use of a lower concentration of the API to achieve the intended therapeutic effect, thereby reducing intrinsic side effects that may be associated with the APIs and improve patient compliance.

BRIEF SUMMARY OF THE INVENTION

The present invention concerns ophthalmic compositions comprising a combination of hyaluronic acid (HA) as a transporting vehicle, and one or more prostaglandin analogues, such as latanoprost, as an active pharmaceutical ingredient (API); and their use for reduction of intraocular pressure to treat or prevent ocular hypertension and glaucoma. The ophthalmic compositions of the invention have improved stability, improved API solubility, and improved efficacy in reducing intraocular pressure.

The present inventor has determined that HA is not an inert viscosity-enhancing polymer, but rather actively contributes to the transport of bioactive agents such as drugs to their place of action. As demonstrated in the Example, 20 micrograms per milliliter of latanoprost dissolved in our HA vehicle is more effective in lowering intraocular pressure than 50 micrograms per milliliter of latanoprost in the "gold standard" XALATAN® drops, which contains the benzalkonium chloride, which is known to transport latanoprost into the eye by comprising the ocular surface barrier.

The present invention provides stable aqueous solutions of prostaglandin analogues without the need for any additives that are not naturally occurring in the human eye. Thus, the ophthalmic compositions are completely biocompatible, and non-sensitizing, making them particularly useful as eye drops for long term use. Furthermore, the HA of the ophthalmic composition enhances the solubility of the prostaglandin analogue contained therein, as demonstrated with latanoprost in the Example.

DETAILED DESCRIPTION OF THE INVENTION

The use of hyaluronic acid (HA) in ophthalmic drug vehicles has been suggested in the literature [3, 10-16]. HA has been shown to have the effect of counteracting the irritating effect of substances to the ocular epithelium [17-20]. When hyaluronic acids of three different molecular weights were investigated using porcine buccal and vaginal tissue and a cell monolayer (Caco-2 cell line), the hyaluronic acid with the lowest molecular weight exhibited increased mucoadhesive performance and the best penetration enhancement with each substrate tested [25].

The inventor proposes that HA is capable of transporting APIs across the ocular epithelial barrier without compromising the ocular surface and its barrier function. The use of HA in drug vehicles will allow for a lower concentration of APIs to achieve the intended therapeutic effect; this will provide an additional reduction of the intrinsic side effects of the APIs. Eye drops comprising HA, as a side-effect free vehicle, have the potential of becoming the platform for the development of the next generation of topical ophthalmic drugs for the treatment of sight-threatening diseases. In particular, HA can replace current penetration enhancers in current eye drop formulations, significantly reducing side effects in long-term topical treatment of ocular hypertension and glaucoma.

The healthy ocular surface epithelium is topographically smooth. The lipid bi-layer plasma membrane of the apical corneal epithelial cells is textured by micropilicae which are lined with an anti-adhesive, water binding, protective glycocalyx (Wilcox M D P et al., [23], particularly FIG. 3 therein, originally published in Gipson I K and P Argueso [24]). The glycocalyx mainly consists of membrane-bound mucins and is covered by a mucoaqueous tear film with water binding, lubricating properties predominantly due to dissolved gel-forming mucin MUC5AC secreted by conjunctival goblet cells [7-9]. The largest of the membrane-bound mucins, MUC16, extends from the apex of micropilicae into the mucoaqueous tear layer and prevents cellular adhesion as well as bacterial adherence and invasion. MUC16 plays not only an important role for the cellular epithelial barrier function, but also contributes to the tight junctions between epithelial cells and thus for the paracellular barrier function.

Without wishing to be bound by theory of mechanism of action as a transporting vehicle, in addition to stabilizing the epithelial barrier function, acting as an anti-inflammatory agent, and promoting intimate contact of the bioactive agent (e.g., API) to the ocular surface, the inventor proposes that HA does one or more of the following: binds to MUC16 in the glycocalyx of the apical epithelial cells; binds to adhesion molecule CD44 on the apical surface of the corneal conjunctive epithelium; binds to the hyaluronan receptor for hyaluronic acid-mediated motility (RHAMM) on the apical surface of the corneal conjunctive epithelium; increases local tissue hydration, enabling temporal cell detachment that may create passages or "highways" allowing for cell migration and transport of the bioactive agents along the paracellular pathway; and binds to the HA receptor for endocytosis (HARE) on the apical surface of the corneal conjunctive epithelium, causing HARE-mediated endocytosis of the bioactive agent into the cytoplasm of the epithelial cells. Regarding the latter proposed mechanism of action, the presence of HARE receptors at the surface of ocular epithelial cells allows them to internalize HA by endocytosis. This is a novel option to transport bioactive agents with HA molecules as a vehicle through the cell membrane of epithelial cells without damaging the cell membrane.

It was determined in a test subject that commercial eye drops containing 50 μg/ml latanoprost induced an average intraocular (IOP) reduction of 3.24 mmHg, whereas the prototype eye drops containing 19 μg/ml latanoprost induced an average IOP reduction of 5.87 mmHg. This finding suggests that the combination of latanoprost and high molecular weight hyaluronan is more efficacious at reducing IOP than latanoprost alone.

In combination with the ability of HA to ameliorate the negative effects of corneotoxic substances [17-20], it is anticipated that patients will benefit from this new technology with HA, particularly those requiring long-term topical treatment of diseases like ocular hypertension or glaucoma, who currently suffer from negative side effects of their treatment.

The properties of hyaluronan in eye drops depend on chain length and concentration. Whereas, the concentration of HA is usually part of the labelling of the finished product, it rarely contains any information about chain length. This makes it very difficult to correlate the performance of different products reported in the literature. The average chain length or molecular mass of hyaluronan molecules is usually determined by gel electrophoresis, size exclusion chromatography, small-angle light scattering, or calculated from intrinsic viscosity [η]. Only the method to determine intrinsic viscosity of hyaluronan has been standardized and published in the European and Japanese Pharmacopoeias [21, 22]. Moreover, the clinical performance of eye drops containing very high molecular weight HA (i.e., having an intrinsic viscosity of 2.5 $m^3$/kg or greater) is different from that of eye drops containing low molecular weight HA (<1.8 $m^3$/kg) to medium molecular weight HA (1.8 $m^3$/kg to less than 2.5 $m^3$/kg).

One aspect of the invention concerns a ophthalmic composition, comprising hyaluronic acid and at least one active ingredient comprising a prostaglandin analogue, wherein the HA acts as a transporting vehicle (transporter) of the prostaglandin analogue into the eye.

In some embodiments, other than the active ingredient(s), the ophthalmic composition contains no substances that are not naturally occurring in the human eye.

In some embodiments, the ophthalmic composition contains no preservatives (is preservative-free).

In some embodiments, the prostaglandin analogue is present at a concentration less than that which is effective to treat and/or prevent ocular hypertension or glaucoma without the HA (i.e., in the absence of HA or with the prostaglandin analogue alone). In some embodiments, the prostaglandin analogue is latanaprost and is present at a concentration of less than 50 micrograms per milliliter (less than 50 μg/mL). In some embodiments, the latanaprost is present at a concentration of less than 0.005% in weight to the total volume of the ophthalmic composition (w/v). In some embodiments, the latanoprost is present at a concentration of less than 30 micrograms per milliliter. In some embodiments, the latanoprost is present at a concentration within the range of about 2 micrograms per milliliter to about 45 micrograms per milliliter, about 10 micrograms per milliliter to about 40 micrograms per milliliter, about 15 micrograms per milliliter to about 25 micrograms per milliliter, or about 20 micrograms per milliliter to about 25 micrograms per milliliter. In some embodiments, the latanoprost is present at a concentration of about 20 micrograms per milliliter.

The prostaglandin analogue may be an F2a analogue such as latanoprost, travoprost bimatoprost, tafluprost prostaglandin F2a-ethanolamide, biatroprost (free acid)-d4, bimatoprost-dj, latanoprost ethylamide, unoprostone, unoprostone isopropylester, or a combination of two or more of the foregoing. In some embodiments, the at least one prostaglandin analogue comprises latanoprost. Latanoprost is a prostaglandin F2-alpha isopropyl ester prodrug (17-phenyl substituted PGF2-alpha), which is hydrolyzed by esterases in the cornea to a biologically active latanoprost acid, which goes on to the anterior tissues (Russo A et al., Clin Ophthalmol. 2008 December; 2 (4): 897-905).

In some embodiments, the prostaglandin analogue comprises latanoprost and the latanoprost is present at a concentration in the range of about 20 micrograms per milliliter to about 25 micrograms per milliliter. In some embodiments, the at least one prostaglandin analogue comprises latanoprost and the latanoprost is present at a concentration of about 20 micrograms per milliliter.

In some embodiments, the prostaglandin analogue is bimatoprost and is present at a concentration of less than 100 micrograms per milliliter (less than 100 μg/mL). In some embodiments, the bimatoprost is present at a concentration of less than 90 micrograms per milliliter. In some embodiments, the bimatoprost is present at a concentration within the range of about 5 micrograms per milliliter to about 90 micrograms per milliliter, about 10 micrograms per milliliter to about 80 micrograms per milliliter, about 20 micrograms per milliliter to about 70 micrograms per milliliter, or about 20 micrograms per milliliter to about 60 micrograms per milliliter. In some embodiments, the bimatoprost is present at a concentration of about 50 micrograms per milliliter.

In some embodiments, the prostaglandin analogue is travoprost and is present at a concentration of less than 30 micrograms per milliliter (less than 30 μg/mL). In some embodiments, the travoprost is present at a concentration of less than 25 micrograms per milliliter. In some embodiments, the travoprost is present at a concentration within the range of about 2 micrograms per milliliter to about 25 micrograms per milliliter, about 3 micrograms per milliliter to about 25 micrograms per milliliter, about 5 micrograms per milliliter to about 20 micrograms per milliliter, or about 10 micrograms per milliliter to about 15 micrograms per milliliter. In some embodiments, the travoprost is present at a concentration of about 15 micrograms per milliliter.

In some embodiments, the prostaglandin analogue is tafluprost and is present at a concentration of less than 15 micrograms per milliliter (less than 15 μg/mL). In some embodiments, the tafluprost is present at a concentration of less than 12 micrograms per milliliter. In some embodiments, the tafluprost is present at a concentration within the range of about 1 microgram per milliliter to about 12 micrograms per milliliter, about 2 micrograms per milliliter to about 10 micrograms per milliliter, about 2 micrograms per milliliter to about 10 micrograms per milliliter, or about 3 micrograms per milliliter to about 9 micrograms per milliliter. In some embodiments, the tafluprost is present at a concentration of about 7.5 micrograms per milliliter.

In some embodiments, the prostaglandin analogue is unoprost and is present at a concentration of less than 1,500 micrograms per milliliter (less than 1,500 μg/mL). In some embodiments, the unoprost is present at a concentration of less than 1,350 micrograms per milliliter. In some embodiments, the unoprost is present at a concentration within the range of about 50 microgram per milliliter to about 1,350 micrograms per milliliter, about 100 micrograms per milliliter to about 1,200 micrograms per milliliter, about 200 micrograms per milliliter to about 1,000 micrograms per milliliter, or about 250 micrograms per milliliter to about 900 micrograms per milliliter. In some embodiments, the unoprost is present at a concentration of about 750 micrograms per milliliter.

Advantageously, the ophthalmic composition is storage stable. In some embodiments, the ophthalmic composition is an aqueous solution that is stable for a period of at least 4 weeks, at least 3 months, or at least 6 months, under one or more of the following conditions: (i) temperature of 15 to 25 degrees C., (ii) temperature of 2 to 8 degrees C., or (iii) temperature of 25 degrees C. at 60% relative humidity.

In some embodiments, the hyaluronic acid has an intrinsic viscosity of at least 2.5 $m^3/kg$. In some embodiments, the hyaluronic acid has an intrinsic viscosity of at least 2.9 $m^3/kg$.

In some embodiments, the hyaluronic acid has a molecular weight of at least 3 million Daltons. In some embodiments, the hyaluronic acid has a molecular weight in the range of 3 million to 4 million Daltons.

In some embodiments, the ophthalmic composition has one, two, three, or all four of the following characteristics:

a) a pH of 5.8-8.5;

b) an osmolarity of 240-330 mosmol/kg;

c) a NaCl concentration of 7.6-10.5 g/l; and/or d) a phosphate concentration of 1.0-1.4 mmol/l.

In some embodiments, the ophthalmic composition is a clear and colourless solution, free from visible impurities.

In some embodiments, the ophthalmic composition is sterile.

In some embodiments, the hyaluronic acid is present in the form of COMFORT SHIELD® preservative-free sodium hyaluronate eye drops.

Optionally, the ophthalmic composition includes a combination of two or more active ingredients that lower intraocular pressure. For example, the ophthalmic composition can include a prostaglandin analogue and an additional agent that reduces intraocular pressure by a mechanism of action different from that of the prostaglandin analogue. In some embodiments, the additional agent is a beta adrenergic blocking agent (e.g., timolol), cholinergic agonist, carbonic anhydrase inhibitor, (e.g., dorzolamide, brinzolamide) or adrenergic receptor blockers (e.g., brimonidine). In some embodiments, the additional agent comprises timolol (e.g., timolol maleate).

The ophthalmic composition may be formulated as an eye drop or eye wash, for example.

Another aspect of the invention is a method for reducing intraocular pressure, or maintaining a reduced intraocular pressure, comprising topically administering the ophthalmic composition of the invention to the ocular surface of the affected eye.

Another aspect of the invention is a method for treating, preventing, or delaying onset of intraocular hypertension or glaucoma in a human subject, comprising topically administering the ophthalmic composition of the invention to an ocular surface of an eye of the subject.

The HA used in the ophthalmic composition and methods of the invention may be high molecular weight HA or "HMWHA". The HMWHA that may be used in the invention refers to hyaluronic acid having an intrinsic viscosity of at least 2.5 $m^3/kg$ (i.e. 2.5 $m^3/kg$ or greater) as determined by the method of the European Pharmacopoeia 9.0, "Sodium Hyaluronate", page 3584 [21]. Briefly, the intrinsic viscosity [η] is calculated by linear least-squares regression analysis using the Martin equation: $\text{Log}_{10}(n_r-1/c)=\log_{10}[\eta]+\kappa[\eta]c$. In some embodiments, the high molecular weight hyaluronic acid has an intrinsic viscosity of at least 2.9 $m^3/kg$ (i.e., 2.9 $m^3/kg$ or greater).

In some embodiments, the hyaluronic acid has a concentration of <0.2% w/v. In some embodiments, the hyaluronic acid has a concentration of 0.1 to 0.19% w/v. In some embodiments, the hyaluronic acid has a concentration of 0.15% w/v.

In some embodiments, the HMWHA fluid has the following composition/characteristics, which correspond to those of COMFORT SHIELD® preservative-free sodium hyaluronate eye drops:

a) a pH of 5.8-8.5;

b) an osmolarity of 240-330 mOsmol/kg;

c) a NaCl concentration of 7.6-10.5 g/l; and/or d) a phosphate concentration of 1.0-1.4 mmol/l.

In some embodiments, the fluid is a clear and colorless solution, free from visible impurities. It is envisaged that the fluid is sterile.

In some embodiments, the fluid according to the invention is COMFORT SHIELD® preservative-free sodium hyaluronate eye drops.

In some embodiments, the HA has a molecular weight of at least 3 million Daltons as calculated by the Mark-Houwink equation. In some embodiments, the HA has a molecular weight in the range of 3 million to 4 million Daltons as calculated by the Mark-Houwink equation.

In some embodiments, the HA is hyaluronan. In some embodiments, the HA is cross-linked. In some embodiments, the HA is non-cross-linked. In some embodiments, the HA is linear. In some embodiments, the HA is non-linear (e.g., branched). In some embodiments, the HA is a derivative of hyaluronan, such as an ester derivative, amide derivative, or sulfated derivative, or a combination of two or more of the foregoing.

Optionally, the ophthalmic compositions may include one or more additional bioactive agents (in addition to the one or more prostaglandin analogues). The methods may include topical administration of one or more additional bioactive agents to the ocular surface in the same composition as the prostaglandin analogue and HA, or in a separate composition from the prostaglandin analogue and HA. The term "bioactive agent" refers to any substance that has an effect on the human or non-human animal subject when administered in an effective amount to affect the tissue. The bioactive agent may be any class of substance such as a drug molecule or biologic (e.g., polypeptide, carbohydrate, glycoprotein, immunoglobulin, nucleic acid), may be natural products or artificially produced, and may act by any mechanism such as pharmacological, immunological, or metabolic. Examples of classes of bioactive agents include substances that modify the pressure of the eye (e.g., enzyme inhibitors) and anti-angiogenic agents.

In some embodiments, the ophthalmic composition is free of preservatives and detergents, such as quaternary ammonium preservative (e.g., benzalkonium chloride (BAK) or cetalkoniumchloride), chlorobutanol, edetate disodium (EDTA), polyquaternarium-1 (e.g., POLYQUAD™ preservative), stabilized oxidizing agent (e.g., stabilized oxychloro complex (e.g., PURITE™ preservative)), ionic-buffered preservative (e.g., SOFZIA™ preservative), polyhexamethylene biguanide (PHMB), sodium perborate (e.g., GENAQUA™ preservative), tyloxapol, and sorbate.

In some embodiments, the ophthalmic composition is at least essentially mucin-free; or in other words having a mucin concentration of <0.3% w/v.

The ophthalmic composition may be administered to the ocular surface of one or both eyes of the subject by any topical administration method. For example, the composition may be administered in fluid form as one or more drops from a device for dispensing eye drops, such as an eye dropper. The composition may be self-administered or administered by a third party (e.g., a care provider or helper). The dosage administered, as single or multiple doses, to an ocular surface will vary depending upon a variety of factors, including patient conditions and characteristics, extent of symptoms, concurrent treatments, frequency of treatment and the effect desired. For example, one or more drops (of, for example, about 30 microliters each) may be administered.

While administration of 1, 2, or 3 drops, one to three times per day, may be sufficient for delivery of the prostaglandin analogue, under some circumstances, more frequent topical co-administration may be needed in some cases. Optionally, upon administration, the subject may close their eyes to keep excess from flowing away from the eye, and optionally a finger may be placed in the corner of the eye to assist with this. Optionally, during administration, the subject may tilt their head back for a period of time (e.g., a minute).

A general aspect of the invention provides a method for reducing intraocular pressure of an eye, comprising topically the ophthalmic composition of the invention to the ocular surface of a subject. A more specific aspect of the invention provides a method for treating, preventing, or delaying the onset or recurrence of ocular hypertension or glaucoma in a subject, comprising topically the ophthalmic composition of the invention to the ocular surface of a human or animal subject. In the methods of the invention, the presence of HA in the ophthalmic compositions allows the use of a lesser concentration of prostaglandin analogue than would otherwise be required for efficacy to reduce intraocular pressure.

In some embodiments, the ophthalmic composition is formulated for topical administration to the ocular surface as an eye drop or eye wash, for example.

In some embodiments, the ophthalmic composition further includes another agent (in combination) that reduces intra-ocular pressure, preferably by a mechanism different from that of the prostaglandin analogue. In some embodiments, the additional agent is a pharmacological agent selected from among a miotic or cholinergic agent (e.g., pilocarpine or eserine), a beta adrenergic antagonist or "beta blocker" (e.g., timolal maleate or betaxolol), an alpha adrenergic agonist (e.g., epinephrine or depiveprine), a carbonic anhydrase inhibitor (e.g., dorzolamide), and a rho kinase inhibitor (e.g., netarsudil), and a prodrug of prostaglandin F2a (e.g., latanoprost).

In some embodiments, the subject to which the ophthalmic condition is topically administered is a child under age 18 (e.g., infant, adolescent, or juvenile). In other embodiments, the subject is an adult. In other embodiments, the subject is over 50 years of age.

For therapeutic embodiments in which the subject has the ocular hypertension or glaucoma at the time of administration, the treatment method may include a step of identifying the subject as one having the ocular hypertension or glaucoma prior to topical administration of the ophthalmic composition. The subject may be identified by diagnosing the subject with the ocular hypertension or glaucoma using one or more tests and/or diagnostic examinations. For example, glaucoma may be detected using one or more of tonometry (measuring intraocular pressure), ophthalmoscopy (examining the optic nerve), perimetry (a visual field test that produces a map of the subject's field of vision, so as to identify areas of vision loss), gonioscopy (determining whether the angle where the iris meets the cornea is open and wide or narrow and closed), and pachymetry (measuring the thickness of the cornea).

Intraocular pressure is the best metric for assessing the status of ocular hypertension or glaucoma and changes therein, such as progression, stabilization, or improvement (Konstas A G et al., *Expert Opinion On Drug Safety,* 2021 April; 20(4):453-466; Kass M A et al., *JAMA Ophthalmol.*

2021; 139(5):558-566; and Allis K et al., *Cureus.* 2020 November; 12(11): e11686). Intraocular pressure may be measured using a Goldmann applanation tonometer, which is the gold standard instrument for measurement of intraocular pressure.

Optionally, the subject is monitored one or more times during and/or after treatment, and results can be compared to previous results to assess status and progress of treatment of the ocular hypertension or glaucoma.

Optionally, the method includes a step of, prior to administration of the ophthalmic composition, identifying the subject as one having one or more signs or symptoms of the ocular hypertension or glaucoma. For example, in the case of glaucoma, the signs and symptoms vary depending on the type and stage of the disorder. For example, in open-angle glaucoma, some signs and symptoms include patchy blind spots in the subject's side (peripheral) or central vision, frequently in both eyes; and tunnel vision in the advanced stages. In acute-angle closure glaucoma, some signs and symptoms include severe headache, eye pain, nausea and vomiting, blurred vision, halos around lights, and eye redness.

Another aspect of the invention concerns a kit that may be used for carrying out the methods of the invention described herein, i.e., the method for reducing intraocular pressure or maintaining a reduced intraocular pressure, and the method for treating, preventing, or delaying the onset or recurrence of intraocular pressure or glaucoma. The kit comprises the ophthalmic composition described herein, and optionally one or more bioactive agents. If included, the bioactive agent may be packaged together with the ophthalmic composition within the same container, separate from the ophthalmic composition, packaged in separate containers. Therefore, the kit may come with one or more bioactive agents in a separate container than the ophthalmic composition, or together in the same container (e.g., "pre-mixed"). Suitable containers include, for example, bottles, vials, syringes, blister pack, etc. The containers may be formed from a variety of materials such as glass or plastic.

The kit may include a delivery agent (separately or in association with the fluid) that is to be brought into contact with the ocular surface or other part of the eye. For example, the kit may include particles (e.g., microparticles or nanoparticles) that are coated with the fluid and/or release the fluid onto the ocular surface.

Optionally, the kit may include a device for dispensing eye drops (e.g., an eye dropper), which may or may not serve as a container for the ophthalmic composition in the kit before the kit's outer packaging is accessed (e.g., opened), i.e., the eye drop dispensing device may function to contain the ophthalmic composition provided in the unaccessed (unopened) kit, or may be empty and receive the fluid after the kit is accessed. Optionally, the kit may include a label or packaging insert with printed or digital instructions for use of the kit, e.g., for carrying out the methods of the invention.

Kits can include packaging material that is compartmentalized to receive one or more containers such as vials, tubes, and the like, each of the container(s) including one of the separate elements to be used in a method described herein. Packaging materials for use in packaging pharmaceutical products include, by way of example only U.S. Pat. Nos. 5,323,907, 5,052,558 and 5,033,252. Examples of pharmaceutical packaging materials include, but are not limited to, blister packs, bottles, tubes, pumps, bags, vials, light-tight sealed containers, syringes, bottles, and any packaging material suitable for a selected formulation and intended mode of administration and treatment.

A kit may include one or more additional containers, each with one or more of various materials desirable from a commercial and user standpoint for use of the compositions described herein. Non-limiting examples of such materials include, but not limited to, buffers, diluents, carrier, package, container, vial and/or tube labels listing contents and/or instructions for use, and package inserts with instructions for use.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In some embodiments of the kit, the ophthalmic composition can be presented in a pack or dispenser device which can contain one or more unit dosage forms containing a composition disclosed herein. The pack can for example contain metal or plastic foil, such as a blister pack. The pack or dispenser device can be accompanied by instructions for administration.

HMWHA Fluid Preparation

In some embodiments, the HA of the ophthalmic composition is HMWHA fluid and has an intrinsic viscosity of at least 2.5 $m^3$/kg (i.e. 2.5 $m^3$/kg or greater) and preferably a concentration of <0.2% w/v. In some embodiments, the hyaluronic acid has an intrinsic viscosity of at least 2.9 $m^3$/kg (2.9 $m^3$/kg or greater).

Viscoelasticity is defined as characteristics of a fluid having both viscous and elastic properties. The zero shear viscosity is determined as the steady shear plateau viscosity at vanishing shear rate. For highly viscous formulations, measurement with a controlled stress rheometer is preferred.

The relation between molecular weight and intrinsic viscosity [η] in $m^3$/kg is given through the Mark-Houwink equation:

$$[\eta]=k\cdot(M_{rm})^a$$

with $M_{rm}$ being the molecular mass in MDa and the coefficients $$k=1.3327\cdot10^{-4}$$

and $$a=0.6691$$

which values for k and a having been found as most predictive.

The HMWHA fluid may be produced by: sterilizing the filling line; adding purified water or water for injection (WFI) to a stainless steel mixing tank; adding salts while mixing; slowly adding HA and mixing until a homogeneous solution/fluid is achieved; optionally, adding one or more bioactive agents such as a prostaglandin analogue; adjusting pH value by adding NaOH or HCl, if required, while continuing the mixing process; transferring the solution over a 1 μm pore size filter cartridge to a sterile holding tank; and aseptically filling the solution via sterile filtration into the sterile primary package (monodose or vial). In the case of monodoses, this may be done by a blow-fill-seal (BFS) process.

Preferably, the HMWHA fluid has at least essentially mucin-free or in other words having a mucin concentration of <0.3% w/v. This means that the flow behavior or properties essentially is reached or adjusted by hyaluronan and not by mucin naturally present in the subject's tear fluid and mainly responsible for the flow behavior thereof.

It is preferred that if substances are added that increase the viscosity, they are added towards, or during, or as a final step. The mixing is carried out so as to reach a homogeneous mixture. As an alternative or in addition, it is preferred to initially provide purified water or water for injection as a basis, and then, optionally, electrolytes, buffers and substances which do not increase the viscosity are added at first to the purified water or water for injection.

HA is further described in the monograph of the European Pharmacopoeia 9.0, page 3583 (Sodium Hyaluronate), which is incorporated herein by reference in its entirety.

In one embodiment, the fluid used in the ophthalmic drug-delivery system (ODS), methods, and kit of the invention has the characteristics listed in Table 1:

TABLE 1

| Characteristic | Specification | Test Method |
|---|---|---|
| Appearance | clear and colorless solution, free from visible impurities | Ph.Eur. |
| pH value | 6.8-7.6 | Ph.Eur. |
| Osmolality | 240-330 mosmol/kg | Ph.Eur. |
| HA concentration | 0.10-0.19 % w/v | Ph.Eur. |
| NaCl concentration | 7.6-10.5 g/l | Ph.Eur. |
| Sterility | Sterile | Ph.Eur. |
| Phosphate concentration | 1.0-1.4 mmol/l | Ph.Eur. |

Definitions

The term "a," "an," "the" and similar terms used in the context of the present invention (especially in the context of the claims) are to be construed to cover both the singular and plural unless otherwise indicated herein or clearly contradicted by the context. Thus, for example, reference to "a cell" or "a bioactive agent" should be construed to cover or encompass both a singular cell or singular bioactive and a plurality of cells and a plurality of bioactive agents unless indicated otherwise or clearly contradicted by the context. Similarly, the word "or" is intended to include "and" unless the context clearly indicates otherwise. The abbreviation, "e.g." is derived from the Latin exempli gratia, and is used herein to indicate a non-limiting example. Thus, the abbreviation "e.g." is synonymous with the term "for example."

The term "co-administer" in the context of the invention refers to topical administration of the ophthalmic composition and one or more other bioactive agents to the ocular surface, simultaneously or consecutively in any order, within the same composition or separate compositions.

The term "effective amount" in the context of the administered fluid of the invention means the amount of fluid necessary to obtain a desired result, such as the amount necessary to transport a bioactive agent into the eye.

The term "isolated," when used as a modifier of a composition, means that the compositions are made by human intervention or are separated from their naturally occurring in vivo environment. Generally, compositions so separated are substantially free of one or more materials with which they normally associate with in nature, for example, one or more protein, nucleic acid, lipid, carbohydrate, cell membrane. A "substantially pure" molecule can be combined with one or more other molecules. Thus, the term "substantially pure" does not exclude combinations of compositions. Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (for nucleic acid and peptide).

As used herein, the term "hyaluronic acid" (HA) refers to the glycosaminoglycan composed of disaccharide repeats of N-acetylglucosamine and glucuronic acid found in nature, also known as hyaluronan (e.g., the straight chain, glycosaminoglycan polymer composed of repeating units of the disaccharide [-D-glucuronic acid-b1,3-N-acetyl-D-glucosamine-b1,4-]n), as well as derivatives of hyaluronan having chemical modifications such as esters of hyaluronan, amide derivatives, alkyl-amine derivatives, low molecular weight and high molecular weight forms of hyaluronans, and cross-linked forms such as hylans. Thus, the disaccharide chain may be linear or non-linear. Hyaluronan can be cross-linked by attaching cross-linkers such as thiols, methacrylates, hexadecylamides, and tyramines. Hyaluronan can also be cross-linked directly with formaldehyde and divinylsulfone. Examples of hylans include, but are not limited to, hylan A, hylan A, hylan B, and hylan G-F 20 (Hargittai M and I Hargittai, "More Conversations with Hyaluronan Scientists," from *Hyaluronan—From Basic Science to Clinical Applications*, Balazs E A, Ed., Vol. 3, 2011, PubMatrix, Edgewater, N J; Cowman M K et al., Carbohydrate Polymers 2000, 41:229-235; Takigami S et al., Carbohydrate Polymers, 1993, 22:153-160; Balazs E A et al., "Hyaluronan, its cross-linked derivative-Hylan- and their medical applications", in Cellulosics Utilization: Research and Rewards in Cellulosics, Proceedings of Nisshinbo International Conference on Cellulosics Utilization in the Near Future (Eds Inagaki, H and Phillips G O), Elsevier Applied Science (1989), NY, pp. 233-241; Koehler L et al., *Scientific Reports,* 2017, 7, article no. 1210; and Pavan M et al., *Carbohydr Polym,* 2013, 97(2): 321-326; which are each incorporated herein by reference in their entirety).

The term "hyaluronic acid" or HA includes HA itself and pharmaceutically acceptable salts thereof, such as sodium hyaluronate. The HA can be formulated into pharmaceutically-acceptable salt forms. Pharmaceutically-acceptable salts of HA can be prepared using conventional techniques.

The term "high molecular weight" or "HMW" in the context of hyaluronic acid of the invention refers to hyaluronic acid having an intrinsic viscosity of at least 2.5 $m^3$/kg (i.e., 2.5 $m^3$/kg or greater) as determined by the method of the European Pharmacopoeia 9.0, "Sodium Hyaluronate", page 3584 (which is incorporated herein by reference in its entirety). Briefly, the intrinsic viscosity [η] is calculated by linear least-squares regression analysis using the Martin equation: $Log_{10}(n_r-1/c)=log_{10}[\eta]+\kappa[\eta]c$. In some embodiments, the high molecular weight hyaluronic acid has an intrinsic viscosity of at least 2.9 $m^3$/kg (i.e., 2.9 $m^3$/kg or greater).

As used herein, the term "ocular disorder" or "eye disorder" is intended broadly to include any abnormality of the eye (e.g., disease, condition, trauma) that may benefit from the co-administered bioactive agent (therapeutically or prophylactically). The disorder may be any stage, and may be an acute disorder or chronic disorder. For example, the HMWHA and bioactive agent may be co-administered at an early stage, intermediate stage, or advanced stage of the eye disorder. The disorder may be of any severity (e.g., mild, moderate, or severe). In some embodiments, the ocular disorder is a disorder of the anterior segment, posterior segment, or both. The ophthalmic composition and methods are useful for treating, preventing, or delaying the onset or recurrence of ocular hypertension and glaucoma.

As used herein, the term "ocular surface" refers to the cornea and conjunctiva, and portions thereof, including the conjunctiva covering the upper and lower lids. The HA and prostaglandin analog may be topically co-administered to one or more parts of the ocular surface, including, for example, the entire ocular surface.

"Pharmaceutically acceptable salt" includes both acid and base addition salts. A pharmaceutically acceptable salt of HA or any one of the other compounds described herein (e.g., prostaglandin analogues and other agents that reduce intraocular pressure) is intended to encompass any and all pharmaceutically suitable salt forms. Preferred pharmaceutically acceptable salts described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al. [29], which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra. In some embodiments, the pharmaceutically acceptable salt is sodium salt (see "Sodium Hyaluronate" at page 3583 of European Pharmacopoeia 9.0, which is incorporated herein by reference).

As used herein, the terms "subject", "patient", and "individual" refer to a human or non-human animal. A subject also refers to, for example, primates (e.g., humans), cows, sheep, goats, horses, dogs, cats, rabbits, rats, mice, fish, birds and the like. In some embodiments, the subject is a mammal. In some embodiments, the subject is a human. In some embodiments, the subject is a bird or fish. Thus, the methods may be carried out in the medical setting and the veterinary setting. The non-human animal subject may be, for example, a pet or an animal model of an ocular or non-ocular disease. In some embodiments, the subject is a human adult. In other embodiments, the subject is a child under age 18 (e.g., infant, adolescent, or juvenile).

The phrase "topical administration" is used herein in its conventional sense to mean topical delivery to the desired anatomical site, such as the ocular surface. The fluid comprising high molecular weight hyaluronic acid may be applied directly or indirectly to the ocular surface by any manner that allows an effective amount of the fluid and ocular surface to make contact. For example, the fluid may be applied directly to the ocular surface, such as via eye drops or lavage, or applied indirectly via a delivery agent (i.e., a fluid delivery agent) that is brought into contact with the ocular surface or other part of the eye. An example of a delivery agent is a particle (e.g., microparticles or nanoparticles) that is coated with the fluid and/or releases the fluid onto the ocular surface. Such particles may be composed of various materials, such as natural or synthetic polymers. In some embodiments, the delivery agent may itself be administered as drops.

The terms "treat", "treating" and "treatment" include alleviating, ameliorating, inhibiting the progress of, reversing or abrogating a medical condition, such as ocular hypertension or glaucoma, or one or more symptoms or complications associated with the condition, and alleviating, ameliorating or eradicating one or more causes of the condition.

The invention is described only exemplarily by the embodiments in the description and drawings and is not limited thereto but rather includes all variations, modifications, substitutions, and combinations the expert may take from the complete documents of this application under consideration of and/or combination with his specific knowledge.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example—Comparison of a Combination of Latanoprost and High Molecular Weight Hyaluronic Acid to Latanoprost Alone in Reduction of Intraocular Pressure

Materials and Methods

Sterile bulk solution for the production of COMFORT SHIELD® MDS eye drops (i.com medical GmbH, Munich, Germany) was used as vehicle for the preparation of prototype latanoprost bulk solution (PLBS). The vehicle contained 0.15% w/v hylan A (HA with 2.9 $m^3$/kg intrinsic viscosity) dissolved in phosphate buffered saline solution (8.035 g/l NaCl; 1.2 mmol/l $Na_2HPO_4/NaH_2PO_4$; pH 7.4). Latanoprost was obtained from Yonsung Fine Chemicals Co. Ltd., Gyeonggi-do, Republic of Korea. PLBS was prepared by medi-pharm Laboratorium GmbH, Falkensee, Germany by dissolving 20±1 µg/ml latanoprost in the vehicle.

Sterile 10 ml bottles with Ophthalmic Squeeze Dispenser (OSD) were obtained from Aptar Radolfzell GmbH, Radolfzell, Germany. Medi-pharm Laboratorium GmbH prepared two batches of prototype latanoprost test samples (PLTS-A) for stability screening by aseptically filling 9 ml of PLBS into Aptar bottles and closing them with the OSD dispenser. Sterile NOVELIA® 11 ml soft bottles and PUREFLOW® 1500 droppers with valve diameter 1.6 were obtained from Nemera, La Verpilliere, France. Pharmpur GmbH, Konigsbrunn, Germany prepared prototype latanoprost test samples (PLTS-N) for the IOP self-test by aseptically filling 10 ml of PLBS into sterile Novelia bottles and closing them with the droppers. These test samples had to be kept vertical to minimize the contact between the solution and the dropper, as latanoprost has tendency to adsorb to silicone parts contained in the dropper. The latanoprost concentration in the PLTS-N bottle used for the self-test was 19 µg/ml.

XALATAN® eye drops (PFIZER OFG Germany GmbH, Berlin, Germany) containing 50 µg/ml latanoprost, 0.2 mg/ml benzalkonium chloride and 6.3 mg/ml phosphates were used as comparative samples in the IOP self-test.

COMFORT SHIELD® MDS 0.15% hylan A eye drops (i.com medical GmbH, Munich, Germany), composed of the vehicle of the prototype latanoprost test samples, were used as control and during the wash-out period of the IOP self-test.

Test Subject

The test subject (TS) is a 71 year old, male, with healthy ocular surface, without history of ocular trauma or ocular surgery or use of preserved eye drops, with untreated ocular hypertension not associated with glaucoma.

Methods

In a pre-test 25 µg/ml and 50 µg/ml latanoprost were added to the vehicle and the solution stirred for 18 hours at 40° C. The latanoprost content was determined by HPLC using a Hypersil B D S C18 5 µg, 150.0×4.0 mm column (VDS optilab) and a UV detector (200 nm). Independent from the starting amount 20.8 µg/ml latanoprost were found to be dissolved in the vehicle as compared to a solubility of 12.9 µg/ml latanoprost in water (PubChem Compound Summary for CID 5311221, Latanoprost. National Center for Biotechnology Information).

Samples from two batches of PLTS-A were stored for six months at ambient room temperature (15-25° C.), at 2-8° C., at 25° C./60% relative humidity (RH), and at 40° C./75% RH. Initially, after 4 weeks, after 3 months, and after 6 months samples were visually inspected for appearance (clarity) and absence of particles, and tested for pH value, latanoprost content, and loss of weight.

Throughout the self-test IOP was measured using a handheld icareHOME Model TA022 rebound tonometer intended for self-use (Icare Finland Oy, Vantaa, Finland) (Liu, J., et al., *Icare Home Tonometer: A Review of Characteristics and Clinical Utility*. Clin Ophthalmol, 2020. 14: p. 4031-4045). Triple measurements were taken and the average value noted.

IOP is known to fluctuate widely during the 24 hour (circadian) period, and, moreover, that the time of the peak of IOP varies from patient to patient (Barkana, Y., et al., *Clinical utility of intraocular pressure monitoring outside of normal office hours in patients with glaucoma*. Arch Ophthalmol, 2006. 124(6): p. 793-7; Mansouri, K., et al., *Review of the measurement and management of 24-hour intraocular pressure in patients with glaucoma*. Surv Ophthalmol, 2020. 65(2): p. 171-186). Less is known about the day to day (interdian) variability of the IOP. Therefore, the TS measured the IOP of both eyes on seven consecutive days at 08:00 (8 a.m.), 11:00 (11 a.m.), 15:00 (3 p.m.), 19:00 (7 p.m.) and 22:00 (10 p.m.). The individual time of peak IOP of the TS (11:00) was chosen for the IOP monitoring throughout the screening test.

Eight weeks before the self-test the TS applied one drop of Comfort Shield eye drops (=vehicle) in each eye in the morning and evening. The self-test lasted over a period of five weeks, and the IOP of both eyes was measured daily at 11:00. In week 1, 3, and 4 the vehicle was applied in the morning and evening. During weeks 2 and 5 the vehicle was only applied in the morning (between 7:00 and 8:00) and one drop of latanoprost eye drops instilled in each eye between 19:00 and 20:00 in the evening. During week 2 XALATAN® eye drops (50 µg/ml latanoprost) were applied, whereas, in week 5 PLTS-N eye drops (19 µg/ml latanoprost) were instilled.

Results

Stability Screening

The results of stability screening for two batches of prototype latanoprost test samples (PLTS-A) are summarized in Tables 2 and 3.

TABLE 2

Results of stability testing on PLTS-A, batch E030219

| storage condition | test parameter | initially | 4 weeks | 3 months | 6 months |
|---|---|---|---|---|---|
| 15-25° C. | appearance | clear | clear | clear | clear |
| | particles | not visible | not visible | not visible | not visible |
| | pH value | 7.06 | 7.02 | 7.01 | 6.25 |
| | latanoprost content (µg/ml) | 20.66 | 20.74 | 20.20 | 20.62 |

TABLE 2-continued

Results of stability testing on PLTS-A, batch E030219

| storage condition | test parameter | initially | 4 weeks | 3 months | 6 months |
|---|---|---|---|---|---|
| | weight loss | 0.00 | 0.19 | 0.71 | 2.55 |
| 2-8° C. | appearance | clear | clear | clear | clear |
| | particles | not visible | not visible | not visible | not visible |
| | pH value | 7.06 | 6.99 | 7.03 | 6.38 |
| | latanoprost content (μg/ml) | 20.66 | 20.56 | 20.68 | 18.68 |
| | weight loss | 0.00 | 0.05 | 0.07 | 0.96 |
| 25° C./60% RH | appearance | clear | clear | clear | clear |
| | particles | not visible | not visible | not visible | not visible |
| | pH value | 7.06 | 7.03 | 6.95 | 6.27 |
| | latanoprost content (μg/ml) | 20.66 | 20.56 | 20.35 | 20.20 |
| | weight loss | 0.00 | 0.37 | 1.78 | 4.80 |
| 40° C./75% RH | appearance | clear | clear | clear | clear |
| | particles | not visible | not visible | not visible | not visible |
| | pH value | 7.06 | 6.96 | 6.66 | 5.81 |
| | latanoprost content (μg/ml) | 20.66 | 18.96 | 18.43 | 11.64 |
| | weight loss | 0.00 | 0.81 | 2.01 | 5.05 |

TABLE 3

Results of stability testing on PLTS-A, batch E040219

| storage condition | test parameter | initially | 4 weeks | 3 months | 6 months |
|---|---|---|---|---|---|
| 15-25° C. | appearance | clear | clear | clear | clear |
| | particles | not visible | not visible | not visible | not visible |
| | pH value | 7.06 | 7.04 | 7.03 | 6.22 |
| | latanoprost content (μg/ml) | 20.88 | 20.30 | 20.15 | 20.11 |
| | weight loss | 0.00 | 0.26 | 0.80 | n.d.* |
| 2-8° C. | appearance | clear | clear | clear | clear |
| | particles | not visible | not visible | not visible | not visible |
| | pH value | 7.06 | 7.10 | 7.07 | 6.36 |
| | latanoprost content (μg/ml) | 20.88 | 20.64 | 20.14 | 19.59 |
| | weight loss | 0.00 | 0.04 | 0.07 | n.d. |
| 25° C./60% RH | appearance | clear | clear | clear | clear |
| | particles | not visible | not visible | not visible | not visible |

TABLE 3-continued

Results of stability testing on PLTS-A, batch E040219

| storage condition | test parameter | initially | 4 weeks | 3 months | 6 months |
|---|---|---|---|---|---|
| | pH value | 7.06 | 7.04 | 6.97 | 6.25 |
| | latanoprost content (μg/ml) | 20.88 | 19.52 | 19.53 | 19.33 |
| | weight loss | 0.00 | 0.31 | 0.84 | n.d. |
| 40° C./75% RH | appearance | clear | clear | clear | clear |
| | particles | not visible | not visible | not visible | not visible |
| | pH value | 7.06 | 6.87 | 6.73 | 5.88 |
| | latanoprost content (μg/ml) | 20.88 | 17.50 | 13.58 | 10.50 |
| | weight loss | 0.00 | 0.61 | 1.61 | n.d. |

*n.d. = not determined

In order to study the individual circadian rhythm and interdian variability the TS performed IOP measurements on seven consecutive days. The IOP of the TS reached a peak in the late morning followed by a continuous decrease until the evening (see Table 4).

TABLE 4

Circadian and interdian variation of IOP in the right (OD) and left eye (OS) of the TS

| | IOP OD in mm Hg | | | | | IOP OS in mm Hg | | | | |
|---|---|---|---|---|---|---|---|---|---|---|
| time | 08:00 | 11:00 | 15:00 | 19:00 | 22:00 | 08:00 | 11:00 | 15:00 | 19:00 | 22:00 |
| day 1 | 27.0 | 29.3 | 26.7 | 24.0 | 22.3 | 25.3 | 28.3 | 25.3 | 23.0 | 22.7 |
| day 2 | 24.7 | 29.3 | 30.0 | 24.7 | 24.3 | 24.7 | 26.3 | 28.7 | 25.7 | 23.0 |
| day 3 | 28.7 | 31.7 | 27.3 | 24.3 | 25.3 | 28.3 | 30.0 | 26.0 | 24.3 | 23.7 |
| day 4 | 25.7 | 29.3 | 25.7 | 24.3 | 24.7 | 25.0 | 27.3 | 26.0 | 23.3 | 23.3 |
| day 5 | 29.7 | 26.3 | 27.7 | 27.3 | 25.7 | 29.3 | 25.7 | 27.7 | 26.0 | 24.7 |
| day 6 | 27.3 | 31.0 | 28.7 | 29.0 | 24.0 | 26.3 | 30.7 | 29.7 | 27.0 | 22.0 |
| day 7 | 25.7 | 29.7 | 28.3 | 25.3 | 26.3 | 25.0 | 30.3 | 29.3 | 25.3 | 26.7 |
| mean IOP | 27.0 | 29.5 | 27.8 | 25.6 | 24.7 | 26.3 | 28.4 | 27.5 | 25.0 | 23.7 |
| standard deviation | 1.8 | 1.7 | 1.4 | 1.9 | 1.3 | 1.8 | 2.0 | 1.8 | 1.5 | 1.5 |

For this reason it was decided to perform IOP measurements at 11:00 for the comparison of the effectiveness of latanoprost eye drops in the eyes of the TS. There were also significant differences from day to day, therefore, IOP measurements with and without latanoprost eye drops were performed on seven consecutive days.

The results of the self-test are summarized in Table 5.

TABLE 5

IOP values before (week 1) and during the application of commercial 50 μg/ml latanoprost eye drops (week 2), and IOP values before (week 4) and during the application of PLTS-N 19 μg/ml lathanoprost eye drops (week 5)

| | IOP in mm Hg | | | | | | | |
|---|---|---|---|---|---|---|---|---|
| | week 1 vehicle | | week 2 lathanoprost 50 μg/ml | | week 4 vehicle | | week 5 PLTS-N 19 μg/ml | |
| | OD | OS | OD | OS | OD | OS | OD | OS |
| day 1 | 24.67 | 26.33 | 23.33 | 25.00 | 26.00 | 27.00 | 22.67 | 23.00 |
| day 2 | 26.33 | 27.67 | 23.00 | 26.00 | 28.67 | 28.00 | 20.67 | 23.00 |
| day 3 | 28.33 | 30.33 | 22.67 | 24.00 | 27.33 | 28.33 | 24.67 | 24.67 |
| day 4 | 27.00 | 28.67 | 23.33 | 24.00 | 22.33 | 24.33 | 19.67 | 20.33 |
| day 5 | 25.67 | 27.67 | 23.67 | 25.67 | 28.00 | 28.67 | 17.00 | 19.33 |
| day 6 | 29.33 | 29.00 | 23.00 | 25.00 | 27.00 | 28.33 | 22.00 | 20.33 |
| day 7 | 27.67 | 28.00 | 26.33 | 26.33 | 29.00 | 29.33 | 20.33 | 22.33 |
| mean IOP | 27.00 | 28.24 | 23.62 | 25.14 | 26.90 | 27.71 | 21.00 | 21.86 |
| standard deviation | 1.60 | 1.26 | 1.24 | 0.92 | 2.26 | 1.65 | 2.44 | 1.91 |

Upon the application of commercial eye drops containing 50 μg/ml latanoprost the intraocular pressure decreased by 3.24 mm Hg from an average baseline value of 27.62 mm Hg to an average value of 24.38 mm Hg, whereas, the prototype latanoprost test sample PLTS-N containing only 19 μg/ml resulted in an IOP decrease of 5.87 mm Hg from an average baseline value of 27.30 mm Hg to an average value of 21.43 mm Hg.

CONCLUSIONS

In the eyes of the test subject (TS), commercial eye drops containing 50 μg/ml latanoprost induced an average IOP reduction of 3.24 mmHg, whereas the prototype eye drops PL20 containing 19 μg/ml latanoprost induced an average IOP reduction of 5.87 mmHg. This finding suggests that the combination of latanoprost and high molecular weight hyaluronan is more efficacious at reducing IOP than latanoprost alone.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Morrison, P. W. and V. V. Khutoryanskiy, Advances in ophthalmic drug delivery. Ther Deliv, 2014. 5(12): p. 1297-315.
2. Moiseev, R. V., et al., Penetration Enhancers in Ocular Drug Delivery. Pharmaceutics, 2019. 11(7).
3. Kaur, I. P. and R. Smitha, Penetration enhancers and ocular bioadhesives: two new avenues for ophthalmic drug delivery. Drug Dev Ind Pharm, 2002. 28(4): p. 353-69.
4. Patel, A., et al., Ocular drug delivery systems: An overview. World J Pharmacol, 2013. 2(2): p. 47-64.
5. Patel, P. B., et al., Ophthalmic Drug Delivery System: Challenges and Approaches. Systematic Reviews in Pharmacy, 2010. 1(2): p. 113-120.
6. Burgalassi, S., et al., Cytotoxicity of potential ocular permeation enhancers evaluated on rabbit and human corneal epithelial cell lines. Toxicol Lett, 2001. 122(1): p. 1-8.
7. Dogru, M., et al., Alterations of the ocular surface epithelial mucins 1, 2, 4 and the tear functions in patients with atopic keratoconjunctivitis. Clin Exp Allergy, 2006. 36(12): p. 1556-65.
8. Dogru, M., et al., Alterations of the ocular surface epithelial MUC16 and goblet cell MIUC5AC in patients with atopic keratoconjunctivitis. Allergy, 2008. 63(10): p. 1324-34.
9. Mantelli, F. and P. Argueso, Functions of ocular surface mucins in health and disease. Curr Opin Allergy Clin Immunol, 2008. 8(5): p. 477-83.
10. Gurny, R., et al., Design and evaluation of controlled release systems for the eye. J Controlled Release, 1987. 6: p. 367-373.
11. Saettone, M. F., et al., Evaluation of muco-adhesive properties and in vivo activity of ophthalmic vihicles based on hyaluronic acid. Int J Pharm, 1989. 51: p. 203-212.
12. Saettone, M. F., et al., Evaluation of high- and low-molecular-weight fractions of sodium hyaluronate and an ionic complex as adjuvants for ophthalmic vehicles containing pilocarpine. Int J Pharm, 1991. 72: p. 131-139.
13. Brown, M. B. and S. A. Jones, Hyaluronic acid: a unique topical vehicle for the localized delivery of drugs to the skin. J Eur Acad Dermatol Venereol, 2005. 19(3): p. 308-18.
14. Liao, Y. H., et al., Hyaluronan: pharmaceutical characterization and drug delivery. Drug Deliv, 2005. 12(6): p. 327-42.
15. Khan, R., B. Mahendhiran, and V. Aroulmoji, Chemistry of hyaluronic acid and its significance in drug delivery strategies: a review. Int J Pharm Sci & Res, 2013. 4(10): p. 3699-3710.
16. Park, K. and J. R. Robinson, Bioadhesive polymers as platforms for oral-controlled drug delivery: method to study bioadhesion. Int J Pharm, 1984. 19(2): p. 107-127.
17. Wysenbeek, Y. S., et al., The effect of sodium hyaluronate on the corneal epithelium. An ultrastructural study. Invest Ophthalmol Vis Sci, 1988. 29(2): p. 194-9.
18. Pauloin, T., et al., Corneal protection with high-molecular-weight hyaluronan against in vitro and in vivo sodium lauryl sulfate-induced toxic effects. Cornea, 2009. 28(9): p. 1032-41.
19. Liu, X., et al., Therapeutic Effects of Sodium Hyaluronate on Ocular Surface Damage Induced by Benzalkonium Chloride Preserved Anti-glaucoma Medications. Chin Med J (Engl), 2015. 128(18): p. 2444-9.
20. Pauloin, T., et al., In vitro modulation of preservative toxicity: high molecular weight hyaluronan decreases apoptosis and oxidative stress induced by benzalkonium chloride. Eur J Pharm Sci, 2008. 34(4-5): p. 263-73.

21. Sodium Hyaluronate—Natrii Hyaluronas, in European Pharmacopoeia (Ph.Eur.) 10th Edition, T. E. P. Commission, Editor. 2019, European Directorate for the Quality of Medicines & Healthcare.
22. Purified Sodium Hyaluronate, in Japanese Pharmacopoeia (JP XVII). 2016, The Ministry of Health, Labour and Welfare. p. 1575-1576.
23. Wilcox M. D. P. et al., TFOS DEWS II Tear Film Report, Ocul Surf, 2017. 15(3):366-403.
24. Gipson, I. K. and P Argueso, Role of Mucins in the Function of the Corneal and Conjunctival Epithelia. International Review of Cytology, 2003. 231:1-49.
25. Sandri, G, et al., Mucoadhesive and penetration enhancement properties of three grades of hyaluronic acid using porcine buccal and vaginal tissue, Caco-2 cell lines, and rat jejunum. J Pharm Pharmacol, 2004. 56(9) 1083-90).
26. Patel A. et al., Ocular drug delivery systems: An overview, World J Pharmacol, 2013. 2(2): 47-64.
27. Fathi M. et al., Hydrogels for ocular delivery and tissue engineering. Bioimpacts, 2015. 5(4):159-164.
28. Baranowski P. et al., Ophthalmic drug dosage forms: characterization and research methods. The Scientific World Journal, 2014. Volume 2014:1-14.
29. Berge S. M. et al., Pharmaceutical Salts, Journal of Pharmaceutical Science, 1997. 66:1-19.

I claim:

1. An ophthalmic composition, comprising hyaluronic acid and latanoprost, wherein the HA acts as a transporting vehicle (transporter) of latanoprost into the eye and latanoprost is present at a concentration of between about 10 micrograms per milliliter and 40 milligrams per milliliter.

2. The ophthalmic composition of claim 1, wherein, other than latanoprost, the ophthalmic composition contains no substances that are not naturally occurring in the human eye.

3. The ophthalmic composition of claim 1, wherein the ophthalmic composition contains no preservatives.

4. The ophthalmic composition of claim 1, wherein latanoprost is present at a concentration of about 15 micrograms per milliliter to about 25 micrograms per milliliter.

5. The ophthalmic composition of claim 1, wherein the prostaglandin analogue is latanoprost and is present at a concentration of about 20 micrograms per milliliter to about 25 micrograms per milliliter.

6. The ophthalmic composition of claim 1, wherein the ophthalmic composition is an aqueous solution that is stable for a period of at least 4 weeks, at least 3 months, or at least 6 months, under one or more of the following conditions: (i) temperature of 15 to 25 degrees C., (ii) temperature of 2 to 8 degrees C., or (iii) temperature of 25 degrees C. at 60% relative humidity.

7. The ophthalmic composition of claim 1, wherein the hyaluronic acid has an intrinsic viscosity of: a) at least 2.5 $m^3/kg$; or b) at least 2.9 $m^3/kg$.

8. The ophthalmic composition of claim 1, wherein the hyaluronic acid has a molecular weight of at least 3 million Daltons.

9. The ophthalmic composition of claim 1, wherein the ophthalmic composition has one, two, three, or all four of the following:

a) a pH of 5.8-8.5;

b) an osmolarity of 240-330 mosmol/kg;

c) a NaCl concentration of 7.6-10.5 g/l; and/or d) a phosphate concentration of 1.0-1.4 mmol/l.

10. The ophthalmic composition of claim 1, wherein the composition comprises an additional agent that reduces intraocular pressure.

11. The ophthalmic composition of claim 10, wherein the additional agent reduces intraocular pressure by a mechanism of action different from that of latanoprost.

12. The ophthalmic composition of claim 11, wherein the additional agent is a beta adrenergic blocking agent, cholinergic agonist, carbonic anhydrase inhibitor, or adrenergic receptor blockers.

13. The ophthalmic composition of claim 12, wherein the additional agent comprises timolol or timolol maleate.

14. The ophthalmic composition of claim 1, wherein the ophthalmic composition is formulated as an eye drop, eye wash, or contact lens.

15. A method for reducing intraocular pressure, or maintaining a reduced intraocular pressure, comprising topically administering the ophthalmic composition of claim 1 to the ocular surface of the eye.

16. A method for treating, preventing, and/or delaying onset or recurrence of intraocular hypertension or glaucoma in a human subject, comprising topically administering the ophthalmic composition of claim 1 to an ocular surface of an eye of the subject.

17. The ophthalmic composition of claim 8, wherein the hyaluronic acid has a molecular weight in the range of 3 million to 4 million Daltons.

* * * * *